United States Patent [19]

Kersey

[11] Patent Number: 5,664,561
[45] Date of Patent: Sep. 9, 1997

[54] HIGH/LOW FLOW ANESTHETIC VAPORIZER

[75] Inventor: Clifford G. Kersey, Oregon, Wis.

[73] Assignee: The BOC Group plc, Windlesham, England

[21] Appl. No.: 533,909

[22] Filed: Sep. 26, 1995

Related U.S. Application Data

[63] Continuation-in-part of Ser. No. 137,209, filed as PCT/GB92/00751 Apr. 24, 1992, abandoned.

[30] Foreign Application Priority Data

Apr. 26, 1991 [GB] United Kingdom ............... 9109023

[51] Int. Cl.⁶ .................. A61M 15/00; A61M 16/10; F23D 11/00; F23D 14/00
[52] U.S. Cl. ............................. 128/203.26; 128/203.16
[58] Field of Search ................. 128/203.12, 203.16, 128/203.17, 203.26, 203.27, 205.11; 261/DIG. 65

[56] References Cited

U.S. PATENT DOCUMENTS

| | | | |
|---|---|---|---|
| 4,015,599 | 4/1977 | Peterson | 128/204.13 |
| 4,576,159 | 3/1986 | Hahn et al. | 128/203.14 |
| 4,611,590 | 9/1986 | Ryschka et al. | 128/203.14 |
| 5,049,317 | 9/1991 | Kiske et al. | 128/203.25 |
| 5,146,915 | 9/1992 | Montgomery | 128/203.12 |
| 5,237,990 | 8/1993 | Psaros et al. | 128/203.12 |

FOREIGN PATENT DOCUMENTS 4105228  8/1992  Germany ................ 128/203.12

*Primary Examiner*—Kimberly L. Asher
*Attorney, Agent, or Firm*—Roger M. Rathbun; Salvatore P. Pace

[57] ABSTRACT

An anesthetic vaporizer having a means of mixing the anesthetic agent with a relatively low flow of carrier gas or a larger amount of carrier gas. A valve is operable by the user to select between the high flow anesthesia where the carrier gas and anesthetic agent are mixed in a mixing chamber and the low flow anesthesia where the carrier gas and anesthetic agent are diverted directly into the patient circuit. Accordingly, the anesthetic vaporizer is usable for high flow anesthesia, however, when used for low flow, the diverted flow allows more rapid response by eliminating the large volume of the mixing chamber.

4 Claims, 1 Drawing Sheet

HIGH/LOW FLOW ANESTHETIC VAPORIZER

RELATED APPLICATIONS

This application is a continuation-in-part of U.S. patent application Ser. No. 08/137,209, filed as PCT/GB92/00751 Apr. 24, 1992, now abandoned.

BACKGROUND OF THE INVENTION

The present invention relates to an anesthetic vaporizer for the supply of an anesthetic agent to a patient.

It is common to administer anesthetic agents supplied as liquids to a patient as a gas, by vaporizing the liquid, and then carrying the vaporized liquid in a carrier gas. The conditions under which the agent is administered in this way depend on a number of factors, including the anesthetic activity of the agent and the quantity of agent which must be administered to the patient. The conditions can vary between extremes of rates of flow of the carrier gas.

A low flow of carrier gas is associated with closed breathing circuit systems where the carrier gas flow rate is determined by the metabolic gas uptake of the patient, which may be as low as 100 ml./min, and where the gas expired by the patient is returned after the carbon dioxide has been removed. The maximum concentration of anesthetic agent vapor which can be carried by the carrier gas is typically around 30% by volume and is determined by the saturated vapor pressure of the agent.

Carrier gas saturated with agent is mixed with the expired gas in the breathing circuit to produce the required concentration of the agent for inhalation. During surgery, it can be desirable to increase the concentration of the agent in the carrier gas supplied to the patient, for example, because of an increase in the uptake of agent by the patient which can cause the concentration of agent supplied to the patient to fall, or to induce a change in the depth of anesthesia. The limitation on the amount of the agent which can be carried by the carrier gas can be overcome by injecting liquid anesthetic agent directly into the breathing circuit, agent vapor being picked up by the carrier gas as it flows over the liquid agent to increase the concentration in the carrier gas as required.

However, it can be difficult to control accurately the variation with time of the concentration of agent which is supplied to the patient since it will depend on the rate at which agent vapor is picked up by the carrier gas. Furthermore, the injection of liquid agent into the breathing circuit can cause a rapid and undesirable increase in the amount of agent supplied to the patient in the event that some of the liquid is received by the patient as liquid, rather that as vapor in the carrier gas.

Medium and high carrier gas flow rates are associated with open and semi-closed breathing circuits where the range of flow rates will be from about 2 to 15 liters/min. The concentration of anesthetic agent in the carrier gas is generally in the range of 0 to 5% by volume and, under these conditions, there is little variation in the agent concentration due to the factors such as an increase in the uptake of agent by the patient.

However, in order to provide a steady output of concentration of agent, it is necessary for large quantities of the agent to be vaporized. This can be achieved by providing a chamber in which the agent is vaporized and mixed with the carrier gas. It is highly preferable that the agent be completely vaporized by the vaporizer since supply of incompletely vaporized agent can lead to accumulation of liquid anesthetic agent in the chamber in which the agent is vaporized and mixed with the carrier gas. This, in turn, can lead to significant fluctuations in the rate at which the agent is administered to a patient; as an agent vaporizes, the effective amount of agent administered to the patient is greater than intended. Furthermore, the collection of liquid agent makes flushing of agent out of the apparatus more difficult.

Unfortunately, however, the use of the aforesaid chamber in which the agent is vaporized and mixed with carrier gas cannot be used when the flow rate of the carrier gas is low, for example less that about 0.8 liters/min., since it exacerbates the problem associated with low flow rate regimes of controlling changes in agent concentrations accurately.

It would obviously be advantageous to have a single machine be used to administer an anesthetic agent to a patient in a carrier gas, whether the flow rate of the carrier gas is low or high, that is, achieve the best of both systems in a single machine, however, the differing requirements as explained, of the two regimes makes this difficult.

In U.S. Pat. No. 4,611,590, there is disclosed an apparatus for adding a liquid anesthetic agent to respiratory gas supplied to a patient, in which the agent is supplied to a chamber in which it is heated to cause vaporization for subsequent supply directly to a patients breathing circuit. Alternatively, the agent can be supplied to a swirl chamber where it is mixed with a carrier gas. From the swirl chamber, the agent with its associated carrier gas is administered directly to the patients circuit. The apparatus therefore provides the possibility either of administering the anesthetic agent carried by a large volume of a carrier gas or directly without any carrier gas. However, the apparatus of that patent requires the use of the combination of a heated chamber, a temperature sensor and a heated conduit to achieve its operating characteristics.

SUMMARY OF THE INVENTION

The present invention provides a versatile anesthetic vaporizer that is capable of supplying an anesthetic agent in which liquid agent is mixed initially with a small quantity of a carrier gas for subsequent administration to a patient, or alternatively, of providing the anesthetic agent after mixing with a larger quantity of a carrier gas. Thus the apparatus may be used in the situation where high flow is used or where low flow is utilized.

In particular, the vaporizer is capable of controlling the vaporization of the liquid anesthetic supplied to the patient whether it is supplied directly to the patient circuit after vaporization or is supplied to the patient circuit after mixing with an additional quantity of carrier gas.

The high/low flow vaporizer of the present invention can thus have the advantage that, when arranged to supply anesthetic agent directly to a patient's breathing circuit with a low carrier gas flow without agent first being mixed with an additional quantity of a carrier gas, the concentration of the agent in the breathing circuit can be adjusted quickly and conveniently and is not dependent on the degree of saturation of carrier gas as would occur in vaporizers in which carrier gas is passed through a quantity of liquid anesthetic agent. This is made possible due to the providing of small quantity of carrier gas for vaporizing the agent after discharge from the main reservoir.

Furthermore, the ability to supply an agent directly to a patients breathing circuit after vaporization has the significant advantage that the response time for a change in concentration of the agent can be kept low. In these respects, the apparatus differs with systems in the prior art in which anesthetic agent is supplied as liquid directly to a patients breathing circuit to be picked up by the carrier gas flowing over it. In such case, the agent concentration in the carrier gas is dependent on the rate at which the agent is picked up by the gas, which is itself dependent on factors such as the degree of saturation and the temperature of the gas.

The apparatus of the present invention can also be used to provide anesthetic agent in a carrier gas which has a high flow rate. In such arrangement, the carrier gas in a first passageway, together with any agent associated with it, is mixed with additional carrier gas flowing in a second passageway, to increase the total amount of gas in which the agent is carried for administration to a patient. This can be an attractive arrangement where the quantity of agent or carrier gas or both to be administered to the patient is high.

In either case, the selection of the high rate mode or the low rate mode is readily made by a valve by which the flow of gas can be selected. Accordingly, the adaptability of the apparatus of the present invention between high and low gas flow administration conditions can be easily facilitated by a simple control of a valve and thus is readily accomplished.

DETAILED DESCRIPTION OF THE PREFERRED EMBODIMENT

Figure 1:
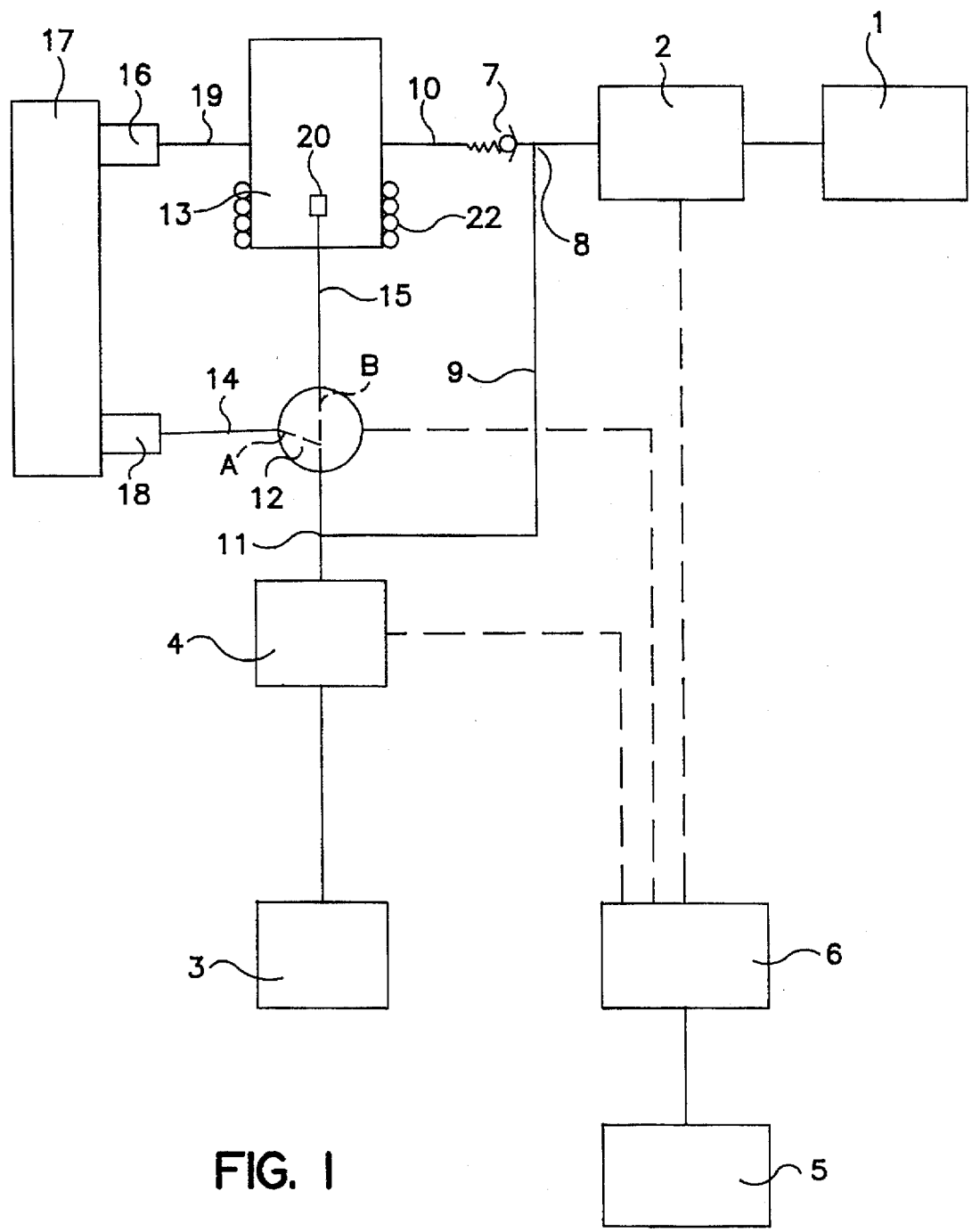
FIG. 1 is a block diagram setting forth the components and flow channels for the present high/low agent vaporizer constructed in accordance with the present invention.

Turning now to FIG. 1, there is shown a block diagram of the high/low flow agent vaporizer constructed in accordance with the present invention. A source 1 of carrier gas is shown and which may consist of, for example, nitrous oxide, oxygen or air, or a combination of those gases. Such source 1 of a carrier gas will generally include an adaptor which can accommodate a number of such separate gases provided in separate containers, generally cylinders which hold the gases under pressure. The source 1 will also normally include appropriate control equipment by which the mixture of the carrier gas which is supplied from it is selected according to the requirements of a patient to whom the carrier gas, together with any associated anesthetic agent, is to be supplied. It will therefore be understood that the selection of a carrier gas formulation is carried out in the present vaporizer prior to the addition to it of anesthetic agent and, indeed, prior to the split of the carrier gas between the various passageways to be described.

The carrier gas from the source 1 proceeds through a flow sensor 2 which may be any conventional sensor to monitor the flow of that carrier gas.

A back pressure regulator 7 is situated downstream of the flow sensor 2 and controls the split of carrier gas at a junction 8 between a first passageway 9 and a second passageway 10. The split of carrier gas between the first and second passageways, 9 and 10, is arranged so that no more that a predetermined quantity of gas flows through the first passageway 9 and so that the excess carrier gas flows through the second passageway 10. The back pressure regulator 7 ensures that only sufficient gas flows through the first passageway 9 to ensure adequate carriage of the anesthetic agent. The quantity of carrier gas which is allowed by the back pressure regulator 7 to flow through the first passageway 9 will be selected to ensure the appropriate degree of atomization or vaporization, or both, of liquid agent to be mixed with that gas.

Preferably, the back pressure regulator 7 is a valve which opens where the pressure exerted against it exceeds a predetermined minimum pressure. An appropriate valve might comprise, for example, an aperture with an appropriate closure member which is biased against the aperture so as to close it, for example, by means of a spring. The closure member may be a ball which acts against a circular aperture in a plate under a force exerted by a spring.

Preferably, the back pressure regulator 7 will allow for a quantity of carrier gas to be selected. For example, the back pressure regulator 7 may be set to ensure that the maximum rate of flow of gas through the first passageway 9 is about 1 liter/min. It has been found that an appropriate back-pressure for many applications is less than about $7.5 \times 10^3$ kg./m$_2$, preferably less than about $5 \times 10^3$ kg./m$_2$. The back pressure may be greater that about $1.5 \times 10^3$ kg./m$_2$, preferably greater than $2.5 \times 10^3$ kg./m$_2$.

A reservoir 3 is provided and which contains the liquid anesthetic agent and which agent is supplied to the first passageway 9 through a dosing pump 4 by which the rate of supply of the anesthetic agent is controlled, according to the required concentration of agent and the required rate of flow of gas into the patient's breathing circuit.

As should be noted, the apparatus of the present invention may include more that one reservoir so that the apparatus can be used to supply a number of different anesthetic agents by appropriate selection of the reservoir from which an agent is to be supplied to the first passageway 9. Different anesthetic agents can require administration to a patient under different conditions and the apparatus of the present invention allows the conditions necessary for administration of each specific agent to be used conveniently.

The mechanism by which the carrier gas in the first passageway 9 and agent which is supplied to it mix can involve atomization of liquid agent, evaporation or a combination of the two. For example, a liquid agent may be broken into small droplets by passing it with a carrier gas through an orifice 20. Subsequently, small droplets of liquid agent may evaporate between the orifice and entry into the patients breathing circuit.

Indeed, in some applications, the evaporation of agent can take place after entry into the patient breathing circuit. This is particularly applicable when the rate of addition of agent to the breathing circuit is relatively high but the rate of flow of carrier gas is low.

The apparatus of the present invention may include additional components by which vaporization or atomization of the liquid agent is encouraged. For example, a heat source or a metal coil 22 (especially a copper coil) may be included to encourage evaporation.

Alternatively, or in addition, a member may be provided with a component which defines an orifice through which the carrier gas and any agent flowing in the first passageway 9 must pass, so that atomization results from the change in pressure as the gas and agent pass out of the orifice. The member may be, for example, a plate having a hole in it, or a length of tube having an internal bore which is smaller than that of the passageway. After passage through such an orifice, liquid agent in the passageway will generally be broken down into small droplets.

Anesthetic agent is preferably added to the carrier gas flowing in the first passageway 9 in such a way that the quantity that is added is controlled continuously and carefully. This may be achieved by means such as a dosing pump 4 such as is shown and described in copending U.S. patent application Ser. No. 07/137,210 filed Oct. 25, 1993 of C.

Kersey and which claims priority from now published application, U.K. Patent Application 9109021.7 the subject matter of which is incorporated herein by reference.

It has been found possible by use of such a pump to control the rate of supply of the anesthetic agent in the range from about 2.0 μliters/min to 11,000 μliters/min. The pump may be made to deliver anesthetic agent at rates which vary by a factor of as much as 5500. For example, the rate of flow of carrier gas through the vaporizer might vary between 0.2 and 15 liters per minute, and the anesthetic concentration might vary between 0.2 and 12% by volume.

As can be seen, the anesthetic agent supplied from the reservoir 3 enters the first passageway 9 at the junction 11 where the anesthetic agent is mixed with the carrier gas. The mixture of carrier gas and agent then flows to a valve 12 which is basically a two position flow valve with both of the positions shown in the drawing. The positions of the valve 12 are indicated as position A and position B. When the valve 12 is in the position A, the gas and liquid anesthetic are routed through a second sub-passageway 14 through which the agent and carrier gas are administered directly into the patient breathing circuit 17 via an outlet 18.

The size of the second sub-passageway 14 through which carrier gas and associated anesthetic agent are administered directly to the patient will generally be selected according to the volumes of fluid to be administered, while maintaining an appropriate passageway in the first passageway 9. The size of the second sub-passageway 14 can usefully be less than that of the first passageway 9. It can be preferred for some applications for the second subpassageway 14 to have an internal diameter of less than about 5 min., more preferably less than about 3.5 mm., for example about 2.0 mm.

The passageways or sub-passageways through which carrier gas and anesthetic agent are administered to the patient through the patient breathing circuit 17 are preferably provided with appropriate fittings so that they can be interfaced appropriately with the patient's breathing circuit 17.

When the valve 12 is in the position B, the vapor and carrier gas mixture flows into first subpassageway 15 to a mixing chamber 13 through a nozzle which insures atomization of the liquid agent, where it is diluted with the excess carrier gas flow which flows from the back pressure regulator 7 through the second passageway 10 and also into the mixing chamber 13. Preferably the nozzle maintains a pressure difference between the first sub-passageway 15 and the mixing chamber 13 and the second passageway 9. A third passageway 19 leads directly from the mixing chamber 13 to the patient breathing circuit 17 through an outlet 16 such that carrier gas from the first and second passageways 9, 10 can be administered to the patient breathing circuit 17 to the patient.

Accordingly, as can now be seen, by control of the valve 12, the high/low flow vaporizer of the present invention can be used for high flow where valve 12 is in position B and a mixing chamber mixes the gas and the vapor before administration to the patient breathing circuit 17 and low flow where the valve is in position A and the liquid anesthetic agent and carrier gas can be directly introduced into the patient breathing circuit 17 to rapidly affect the concentration to the patient.

Control of the valve 12 can be by conventional means such as with a CPU 6 which receives information as to the flow of the carrier gas from the flow sensor 2 and can effect the control of the dosing pump 4 to change the quantity of liquid agent introduced into the system and thereby control the valve 12. The selection of the concentration desired to the patient can be set by a user by an input device 5 such as a dial, or keyboard to establish that concentration. Once set by the user, the CPU 6 can determine the proper setting of the dosing pump and the valve 12 depending upon the flow sensed by the flow sensor 2.

While the invention has been disclosed and described with respect to a single embodiment, it will become apparent that variations and modifications may be made therein, and it is therefore intended in the following claims to cover each such variation and modification as falls within the true spirit and scope of the invention.

I claim:

1. An anaesthetic vaporizer for delivering a mixture of carrier gas and anaesthetic agent to a patients breathing circuit, said anaesthetic vaporizer comprising:

an inlet for receiving carrier gas from a source of carrier gas;

a first passageway within said vaporizer for receiving carrier gas from said inlet;

a gas regulator controlling the flow of carrier gas within said first passageway to a predetermined limited flow;

a reservoir within said vaporizer for containing a supply of liquid anaesthetic agent, said reservoir providing said anaesthetic agent into said first passageway to mix in said first passageway with the carrier gas flowing therein;

a second passageway receiving carrier gas from said inlet through said regulator;

a mixing chamber receiving and mixing carrier gas from said second passageway and the mixed carrier gas and anaesthetic agent from said first passageway;

a third passageway adapted to deliver the mixed carrier gas and anesthetic agent from said mixing chamber to a patients breathing circuit; and a valve means in said first passageway selectively operable to divert carrier gas and anesthetic agent upstream of said mixing chamber, said valve means adapted to deliver the carrier gas and anesthetic agent directly to a patients breathing circuit.

2. An anesthetic vaporizer as defined in claim 1 further including a source of heat by which vaporization of anesthetic agent can be encouraged.

3. An anesthetic vaporizer as defined in claim 1 which includes a component that defines an orifice through which the carrier gas and any anesthetic agent carried with the carrier gas must pass to cause atomization of the agent.

4. An anesthetic vaporizer as defined in claim 1 wherein said gas regulator is a back-pressure valve.

* * * * *